(12) United States Patent
Brannigan

(10) Patent No.: US 6,409,693 B1
(45) Date of Patent: Jun. 25, 2002

(54) LEG SUPPORT DEVICE

(76) Inventor: Robert J. Brannigan, P.O. Box #286, Pequannock, NJ (US) 07440

( * ) Notice: Subject to any disclaimer, the term of this patent is extended or adjusted under 35 U.S.C. 154(b) by 0 days.

(21) Appl. No.: 09/765,459

(22) Filed: Jan. 22, 2001

(51) Int. Cl.$^7$ ............................................. A61F 5/00
(52) U.S. Cl. ........................... 602/16; 602/23; 128/882
(58) Field of Search ........................... 128/869, 882; 602/5, 16, 23, 26

(56) References Cited

U.S. PATENT DOCUMENTS

| | | | |
|---|---|---|---|
| 40,301 A | 10/1863 | Whittlesey | |
| 2,827,897 A | 3/1958 | Pawlowski | |
| 3,928,872 A | * 12/1975 | Johnson | 602/16 |
| 4,408,600 A | * 10/1983 | Davis | 602/16 |
| 4,632,096 A | * 12/1986 | Harris | 602/16 |
| 406,328 A | 7/1989 | Yagn | |
| 4,872,665 A | 10/1989 | Chareire | |
| 5,178,595 A | 1/1993 | Macgregor | |
| 5,383,845 A | * 1/1995 | Nebolon | 602/16 |
| D362,506 S | 9/1995 | Bieri | |

* cited by examiner

Primary Examiner—Michael A. Brown

(57) ABSTRACT

A leg support device for assisting the muscles of the leg used to straighten the leg. The leg support device includes a pair of coupling members for positioning around a leg. A first of the coupling members is positionable on the leg above the knee and a second of the coupling members is positionable below the knee. A pair of biasing members biases the first coupling member away from the second coupling member. Each of the biasing members is securely attached to and extends between one of the first and second coupling members such that each of the biasing members is positioned adjacent to one of the lateral sides of the leg when the coupling members are positioned on the leg.

9 Claims, 6 Drawing Sheets

LEG SUPPORT DEVICE

BACKGROUND OF THE INVENTION

1. Field of the Invention

The present invention relates to knee braces and more particularly pertains to a new leg support device for assisting the muscles of the leg used to straighten the leg.

2. Description of the Prior Art

The use of knee braces is known in the prior art. More specifically, knee braces heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 2,827,897; 406, 328; 4,872,665; 5,178,595; 40,301; and U.S. Des. Pat. No. 362,506.

While these devices fulfill their respective, particular objectives and requirements, the aforementioned patents do not disclose a new leg support device. The inventive device includes a pair of coupling members for positioning around a leg. A first of the coupling members is positionable on the leg above the knee and a second of the coupling members is positionable below the knee. A pair of biasing members biases the first coupling member away from the second coupling member. Each of the biasing members is securely attached to and extends between one of the first and second coupling members such that each of the biasing members is positioned adjacent to one of the lateral sides of the leg when the coupling members are positioned on the leg.

In these respects, the leg support device according to the present invention substantially departs from the conventional concepts and designs of the prior art, and in so doing provides an apparatus primarily developed for the purpose of assisting the muscles of the leg used to straighten the leg.

SUMMARY OF THE INVENTION

In view of the foregoing disadvantages inherent in the known types of knee braces now present in the prior art, the present invention provides a new leg support device construction wherein the same can be utilized for assisting the muscles of the leg used to straighten the leg.

The general purpose of the present invention, which will be described subsequently in greater detail, is to provide a new leg support device apparatus and method which has many of the advantages of the knee braces mentioned heretofore and many novel features that result in a new leg support device which is not anticipated, rendered obvious, suggested, or even implied by any of the prior art knee braces, either alone or in any combination thereof.

To attain this, the present invention generally comprises a pair of coupling members for positioning around a leg. A first of the coupling members is positionable on the leg above the knee and a second of the coupling members is positionable below the knee. A pair of biasing members biases the first coupling member away from the second coupling member. Each of the biasing members is securely attached to and extends between one of the first and second coupling members such that each of the biasing members is positioned adjacent to one of the lateral sides of the leg when the coupling members are positioned on the leg.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new leg support device apparatus and method which has many of the advantages of the knee braces mentioned heretofore and many novel features that result in a new leg support device which is not anticipated, rendered obvious, suggested, or even implied by any of the prior art knee braces, either alone or in any combination thereof.

It is another object of the present invention to provide a new leg support device which may be easily and efficiently manufactured and marketed.

It is a further object of the present invention to provide a new leg support device which is of a durable and reliable construction.

An even further object of the present invention is to provide a new leg support device which is susceptible of a low cost of manufacture with regard to both materials and labor, and which accordingly is then susceptible of low prices of sale to the consuming public, thereby making such leg support device economically available to the buying public.

Still yet another object of the present invention is to provide a new leg support device which provides in the apparatuses and methods of the prior art some of the advantages thereof, while simultaneously overcoming some of the disadvantages normally associated therewith.

Still another object of the present invention is to provide a new leg support device for assisting the muscles of the leg used to straighten the leg.

Yet another object of the present invention is to provide a new leg support device which includes a pair of coupling members for positioning around a leg. A first of the coupling members is positionable on the leg above the knee and a second of the coupling members is positionable below the knee. A pair of biasing members biases the first coupling member away from the second coupling member. Each of the biasing members is securely attached to and extends between one of the first and second coupling members such that each of the biasing members is positioned adjacent to one of the lateral sides of the leg when the coupling members are positioned on the leg.

Still yet another object of the present invention is to provide a new leg support device that allows a user to remain in a bent-leg position for extended periods of time with less muscle and knee strain by placing the stress on the legs.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
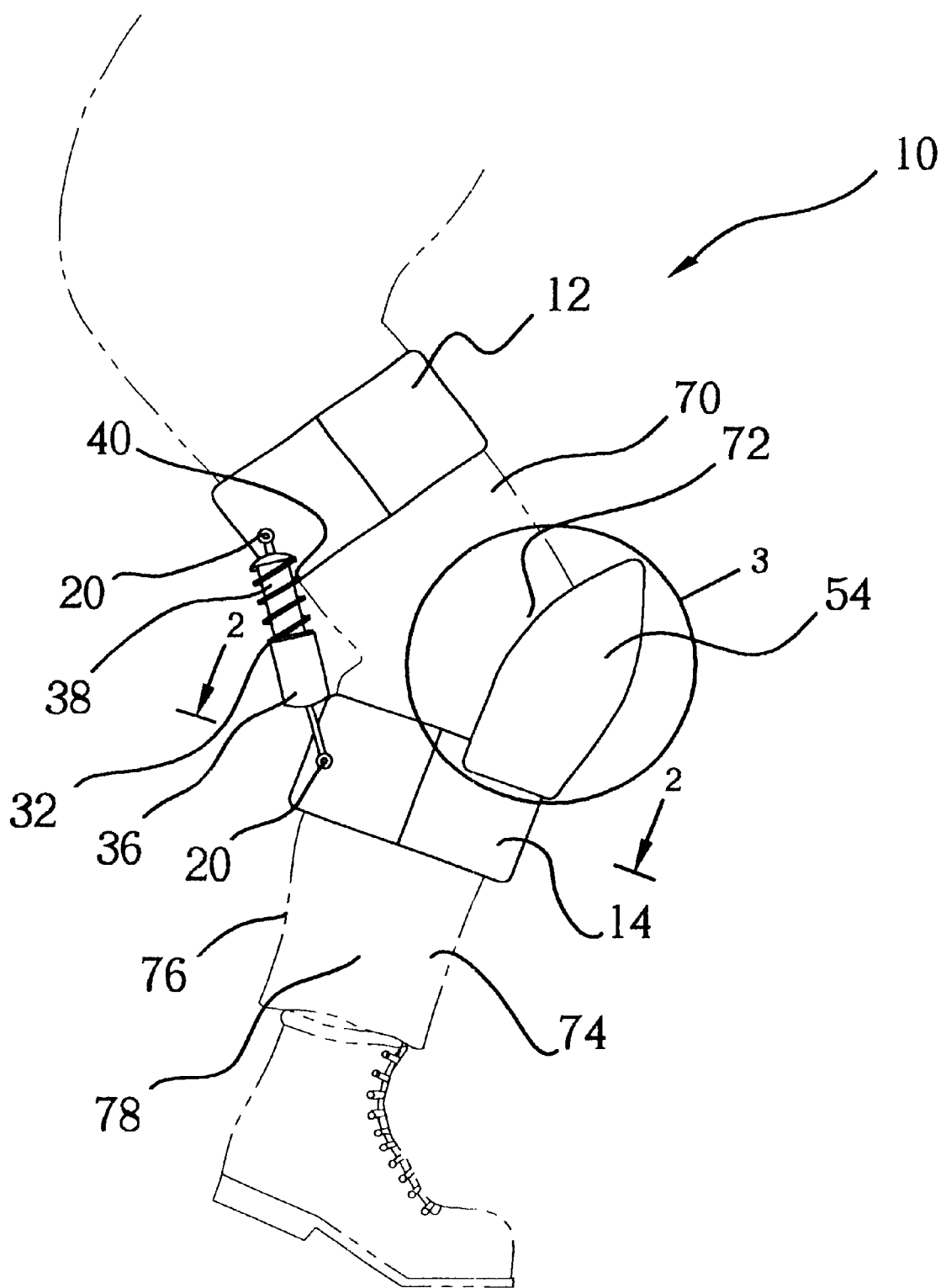
FIG. 1 is a schematic side view of a new leg support device according to the present invention.
Figure 2:
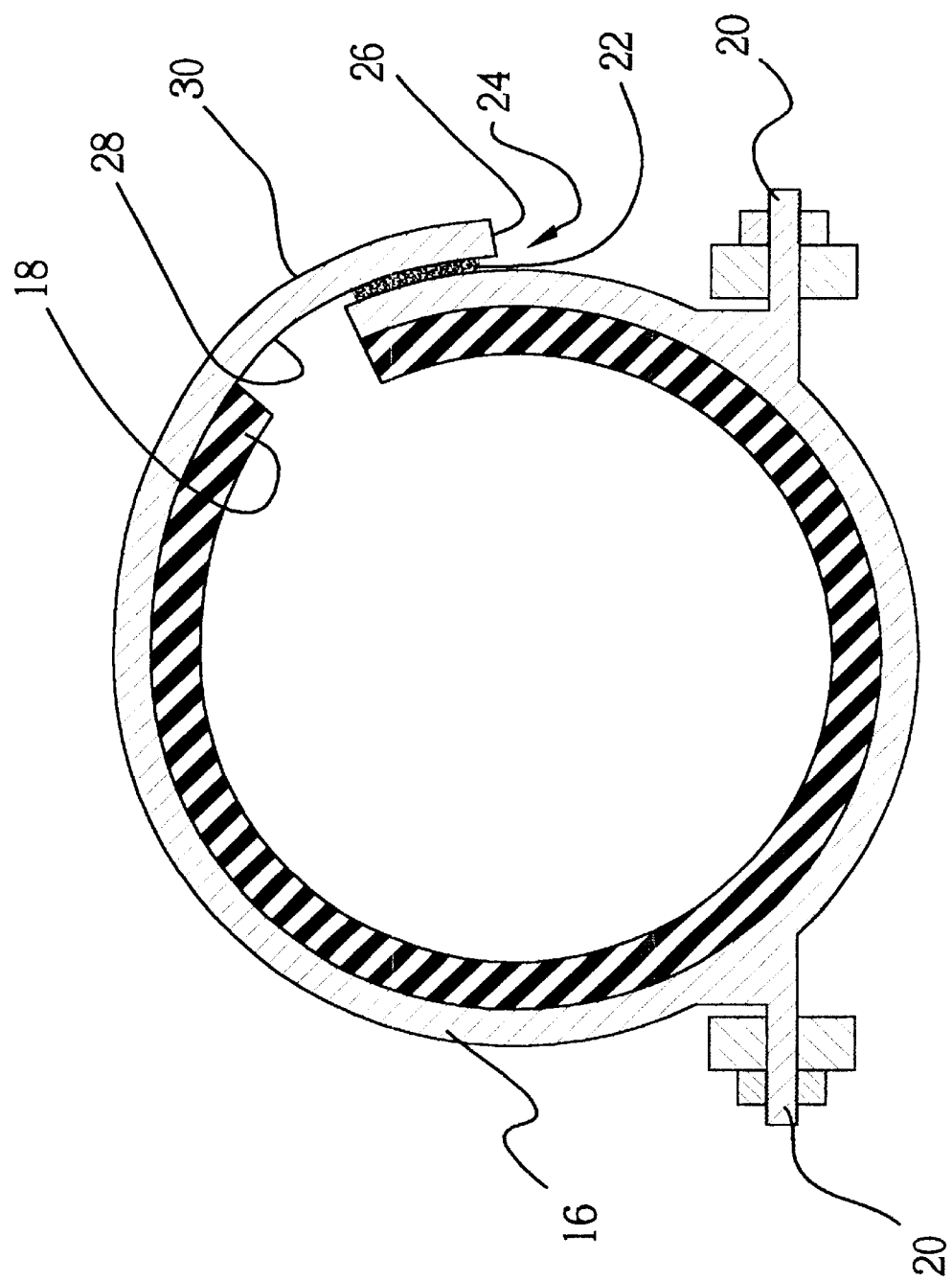
FIG. 2 is a schematic cross-sectional view taken along line 2—2 of the present invention.
Figure 3:
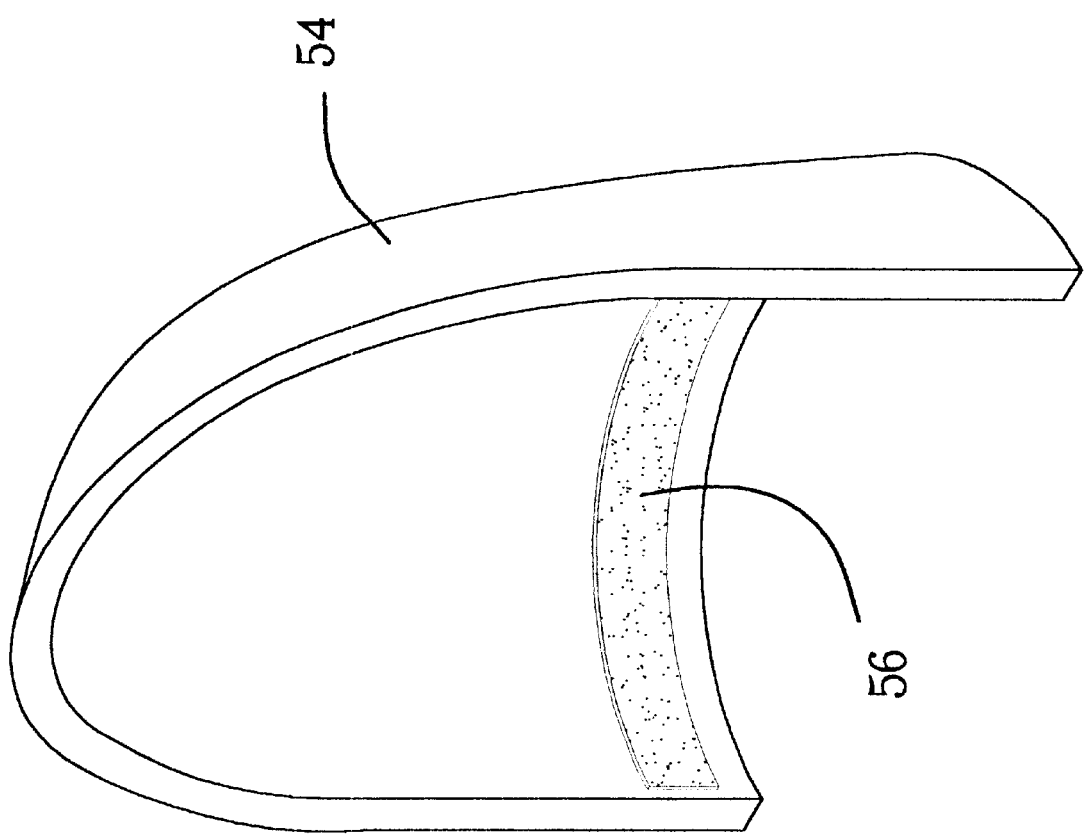
FIG. 3 is a schematic perspective view of the knee pad of the present invention.

With reference now to the drawings, and in particular to FIGS. 1 through 6 thereof, a new leg support device embodying the principles and concepts of the present invention and generally designated by the reference numeral 10 will be described.

As best illustrated in FIGS. 1 through 6, the leg support device 10 generally comprises a device positionable on a leg 70 of a user. The device is removably securable above and below a knee 72 portion of the leg 70. The leg 70 has a front side 74, a back side 76 and a pair of lateral sides 78. The device 10 includes a pair of coupling members 12, 14 for positioning around the leg 70. Each of the coupling members 12, 14 includes an annular member 16, a panel 18, a pair of brackets 20, and a securing means 22.

The annular member 16 has a break 24 therein such that a pair of free ends 26 of the annular member 16 are defined. The annular 16 member has an inner surface 28 and an outer surface 30. The annular member 16 preferably comprises a resiliently flexible material such as a plastic.

The panel 18 is securely attached to and substantially covers the inner surface 28 of the annular member 16. The panel 18 preferably comprises an elastomeric material and acts as padding between the annular member 16 and the leg 70.

Each of the pair of brackets 20 is integrally coupled to and extends outwardly away from the outer surface 30 of the annular member 16. The brackets 20 are generally positioned opposite of each other.

The securing means 22 selectively closes the break 24 in the annular member. The securing means 22 ideally comprises a hook and loop securing means having a hook portion securely attached to the outer surface 30 of the annular member and a loop portion securely attached to the inner surface 28 of the annular member. Each of the hook and loop portions is positioned generally adjacent to one of the free ends 26 of the annular member 16.

A first of the coupling members 12 is positionable on the leg 70 above the knee 72 and a second of the coupling members 14 is positionable on the leg 70 below the knee 72 such that each of the brackets 20 extends outwardly from the lateral sides 78 of the leg 70.

Figure 5:
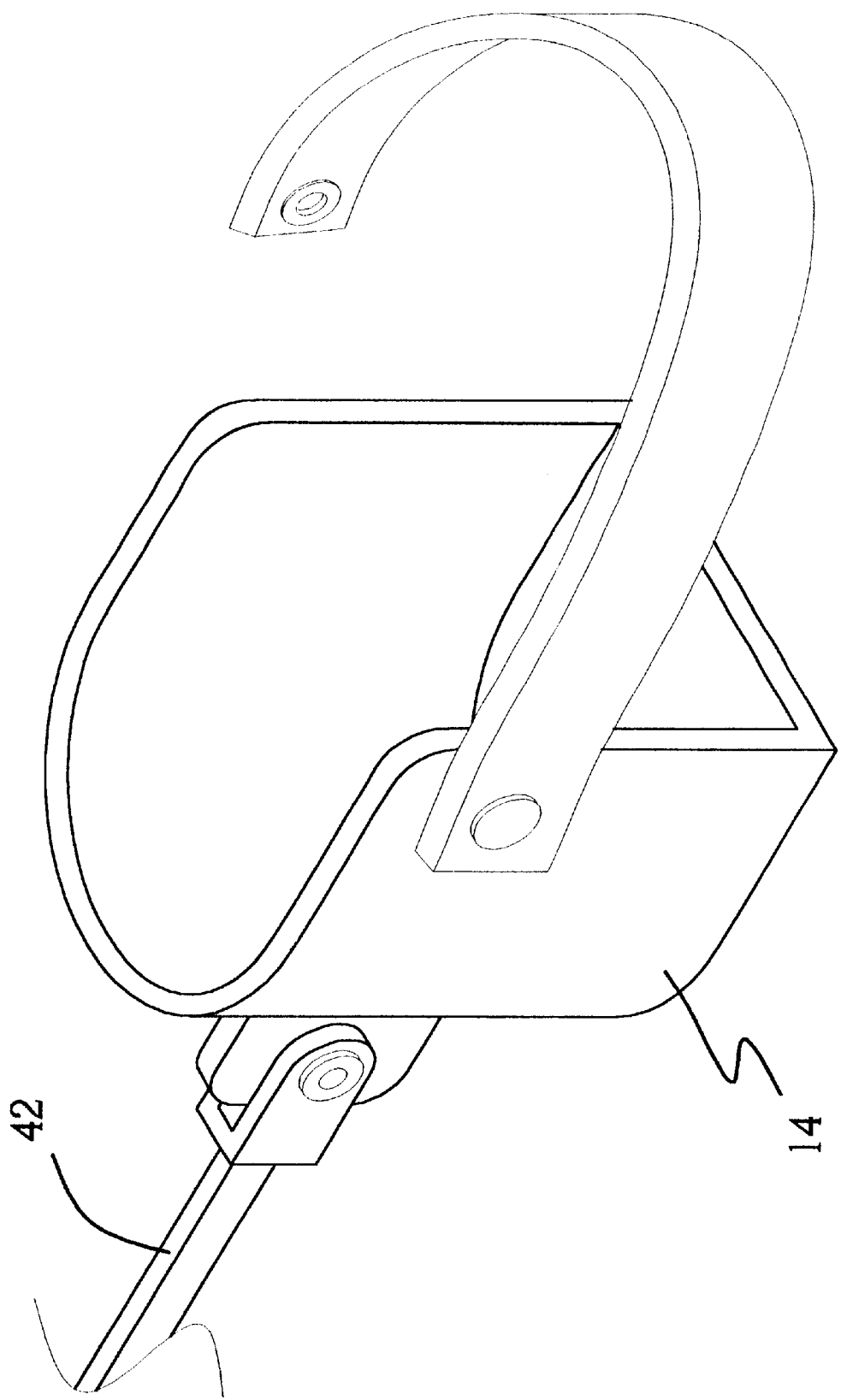
FIG. 5 is a schematic perspective view of the second embodiment's second coupler of the present invention.
Figure 6:
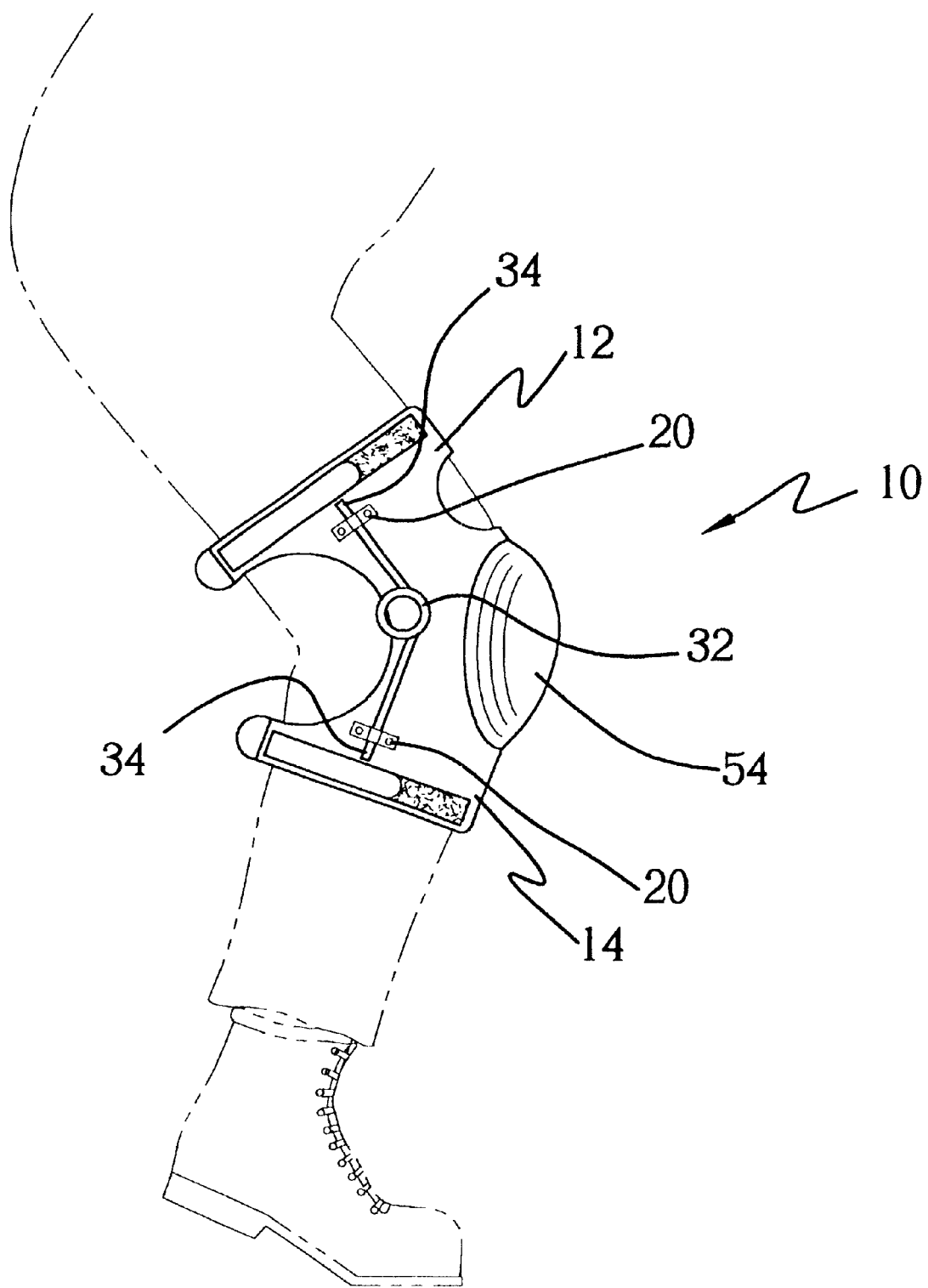
FIG. 6 is a schematic side view of the present invention.

A pair of biasing members 32 biases the first coupling member 12 away from the second coupling member 14. Each of the biasing members 32 is securely attached to and extends between one of the brackets 20 on the first 12 and second 14 coupling members such that each of the biasing members 32 is positioned adjacent to one of the lateral sides 78 of the leg 70 when the coupling members 12, 14 are positioned on the leg 70. The biasing members 32 each preferably includes a coiled spring having two ends 34 extending in opposite directions as shown in FIG. 5. Each of the ends 34 of the spring is attached to one of the brackets 20. Alternatively, the biasing member 32 may comprise a cylinder 36 coupled to one bracket 20 and a piston 38 coupled to the other bracket 20. The piston 38 is movably extendable into the cylinder 36 and a spring 40 positioned around the piston 38 biases the piston 36 outwardly of the cylinder 38 as shown in FIG. 1.

Figure 4:
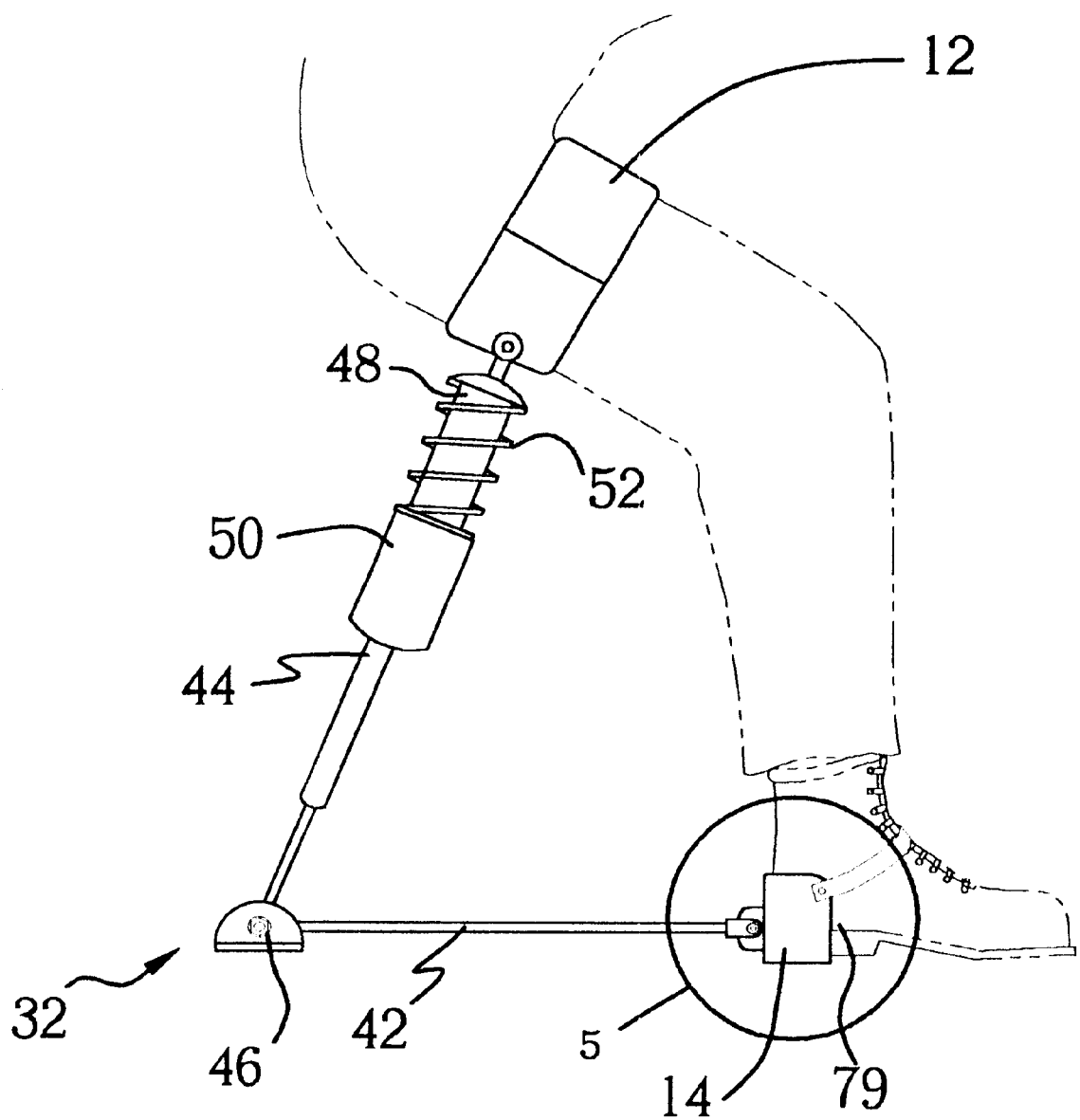
FIG. 4 is a schematic side view of the second embodiment of the present invention.

FIG. 4 shows a second embodiment including a first coupling member 12 positionable around a leg and a second coupling member 14 positionable about a shoe or heel 79. The second coupling member 14 includes a cup portion for positioning around the heel 79. The biasing member 32 consists of a first rod 42 extending from the second coupling member 14 and second rod 44 extending from the first coupling member 12. The rods 42, 44 each have a free end hingedly coupled to a foot 46. The second rod 44 includes a piston 48 movably extendable into a cylinder 50 wherein the piston 48 is urged outward of the cylinder 50 by a spring 52. The foot 46 is positionable on a ground surface behind the leg 70.

A knee pad 54 is securely coupled to and extends between the first 12 and second 14 coupling members. The knee pad 54 is positioned such that the knee pad 54 abuts the knee 72 of the leg 70 when the coupling members 12, 14 are coupled to the leg 70. FIG. 1 depicts a knee pad 54 coupled only to the second coupling 14 member by an adhesive 56 located on the knee pad 54.

In use, the coupling members 12, 14 are coupled to the leg 70 as shown in FIG. 1. The biasing members 32 offer additional support to the knees 72 when a user has their knees in a bent position for an extended period of time by assisting the muscles of the leg used to straighten the leg 70.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A leg brace device, said device being positionable on a leg of a user, the device being removably securable above and below a knee portion of the leg, said leg having a front side, a back side and a pair of lateral sides, said device comprising:
    a pair of coupling members for positioning around the leg, wherein a first of said coupling members is positionable on the leg above the knee and a second of said coupling members is positionable below the knee; and
    a pair of biasing members for biasing said first coupling member away from said second coupling member, each of said biasing members being securely attached to and extending between one of said first and second coupling members such that each of said biasing members is positioned adjacent to one of said lateral sides of said leg when said coupling members are positioned on said leg;
    wherein each of said coupling members comprises:
    an annular member having a break therein such that a pair of free ends of said annular are defined, said annular member having an inner surface and an outer surface, said annular member comprising a resiliently flexible material;
    a panel being securely attached to and substantially covering said inner surface of said annular member, said panel comprising an elastomeric material;
    each of a pair of brackets being integrally coupled to and extending outwardly away from said outer surface of said annular member, said brackets being generally positioned opposite of each other such that each of the brackets extends outwardly from said lateral sides of said leg;
    each of said biasing members being securely attached to and extending between one of said brackets on said first and second coupling members; and
    a securing means for selectively closing said break in said annular member.

2. The leg brace device as in claim 1, wherein each of said coupling members comprises:
    an annular member having a break therein such that a pair of free ends of said annular are defined, said annular member having an inner surface and an outer surface, said annular member comprising a resiliently flexible material.

3. The leg brace device as in claim 2, wherein each of said coupling members further includes:
    a panel being securely attached to and substantially covering said inner surface of said annular member, said panel comprising an elastomeric material.

4. The leg brace device as in claim 2, wherein each of said coupling member further includes:
    each of a pair of brackets being integrally coupled to and extending outwardly away from said outer surface of said annular member, said brackets being generally positioned opposite of each other such that each of the brackets extends outwardly from said lateral sides of said leg; and
    each of said biasing members being securely attached to and extending between one of said brackets on said first and second coupling members.

5. The leg brace device as in claim 2, wherein each of said coupling members further includes:
    a securing means for selectively closing said break in said annular member.

6. The leg brace device as in claim 1, wherein said securing means comprises a hook and loop securing means having a hook portion securely attached to said outer surface of said annular member and a loop portion securely attached to said inner surface of said annular member, each of said hook and loop portions being positioned generally adjacent to one of said free ends of said annular member.

7. The leg brace device as in claim 1, further including:
    a knee pad, said knee pad being securely coupled to said second coupling member, said knee pad being positioned such that said knee pad abuts the knee of the leg when said coupling members are coupled to the leg.

8. A leg brace device, said device being positionable on a leg of a user, the device being removably securable above and below a knee portion of the leg, said leg having a front side, a back side and a pair of lateral sides, said device comprising:
    a pair of coupling members for positioning around the leg, a first of said coupling members is positionable around the leg and a second of said coupling members is positionable about a heel portion of the leg, the second coupling member includes a cup portion for positioning around a heel; and
    a pair of biasing member for biases said first coupling member away from said second coupling member, the biasing member consisting of a first rod extending from the second coupling member and a second rod extending from the first coupling member, the rods each having a free end hingedly coupled to a foot, the second rod including a piston movably extendable into a cylinder wherein the piston is urged outward of the cylinder by a spring, the foot being positionable on a ground surface.

9. A leg brace device, said device being positionable on a leg of a user, the device being removably securable above and below a knee portion of the leg, said leg having a front side, a back side and a pair of lateral sides, said device comprising:
    a pair of coupling members for positioning around the leg, each of said coupling members comprising;
    an annular member having a break therein such that a pair of free ends of said annular member are defined, said annular member having an inner surface and an outer surface, said annular member comprising a resiliently flexible material;
    a panel being securely attached to and substantially covering said inner surface of said annular member, said panel comprising an elastomeric material;
    each of a pair of brackets being integrally coupled to and extending outwardly away from said outer surface of said annular member, said brackets being generally positioned opposite of each other;
    a securing means for selectively closing said break in said annular member, said securing means comprising a hook and loop securing means having a hook portion securely attached to said outer surface of said annular member and a loop portion securely attached to said inner surface of said annular member, each of said hook and loop portions being positioned generally adjacent to one of said free ends of said annular member;

wherein a first of said coupling members is positioned on the leg above the knee and a second of said coupling members is positionable on the leg below the knee such that each of the brackets extend outwardly from said lateral sides of said leg;

a pair of biasing members for biasing said first coupling member away from said second coupling member, each of said biasing members being securely attached to and extending between one of said brackets on said first and second coupling members such that each of said biasing members is positioned adjacent to one of said lateral sides of said leg when said coupling members are positioned on said leg, each of the biasing members include a coiled spring having two ends extending in opposite directions, each of the ends of the spring are attached to one of the brackets; and a knee pad, said knee pad being securely coupled to and extending between said first and second coupling members, said knee pad being positioned such that said knee pad abuts the knee of the leg when said coupling members are coupled to the leg.

* * * * *